United States Patent [19]

Burgio et al.

[11] Patent Number: 5,038,755

[45] Date of Patent: Aug. 13, 1991

[54] APPARATUS FOR PERFORMING MEDICAL EXAMINATIONS ON SMALL CHILDREN

[76] Inventors: Paul A. Burgio, 4279 Brigadoon, Shoreview, Minn. 55126; C. Randall Nelms, Jr., 15 Ridge Rd., North Oaks, St. Paul, Minn. 55127

[21] Appl. No.: 546,090

[22] Filed: Jun. 29, 1990

[51] Int. Cl.$^5$ .............................................. A61B 1/22
[52] U.S. Cl. .......................................... 128/9; 446/72
[58] Field of Search .................. 128/9; 446/72, 73, 74

[56] References Cited

U.S. PATENT DOCUMENTS 1,686,041 10/1928 Smith ...................................... 128/9
2,485,766 10/1949 Parcher .................................... 129/9
3,299,891 1/1967 Smeton .............................. 446/74 X Primary Examiner—William H. Grieb
Attorney, Agent, or Firm—Merchant, Gould, Smith, Edell, Welter & Schmidt

[57] ABSTRACT

An otoscope for performing ear examinations on small children includes a handle portion, a viewing head and a speculum in addition to a toy-like object for distracting the child prior to or during the examination. The toy-like object may resemble an animal, such as a bear, dog or pig. The otoscope will appear less foreign and threatening to small children than those which are presently being used. As a result, an ear examination with the improved otoscope can be performed more safely and efficiently than was heretofore possible.

13 Claims, 5 Drawing Sheets

APPARATUS FOR PERFORMING MEDICAL EXAMINATIONS ON SMALL CHILDREN

BACKGROUND OF THE INVENTION

1. Field of the Invention

This invention relates to devices which are used to perform routine medical examinations on children. More specifically, this invention relates to an improved otoscope for performing ear examinations on children.

2. Description of the Prior Art

Otoscopes and other medical instruments have been in existence for some time. The appearance of a medical instrument, while fulfilling the function of the instrument, can also be useful in instilling psychological security in a patient. Instruments are therefore usually designed to look as professional and sanitary as possible. Adult patients are often anxious about the quality and sterility of their medical care, and the austere professional appearance of the medical instruments is useful in quieting their anxieties. Less anxious patients tend to be more cooperative during examination and treatment. Less anxious patients also have a better mental attitude toward their treatment and may heal more quickly. Due to human psychology, the physical appearance of medical instruments is a very important element of medical care.

Child patients have different anxieties than adult patients. Because children have a wider range of psychological responses to their medical treatment, instilling a good mental attitude in the patient is even more important when treating children. A child is usually very anxious about the friendliness and concern he or she will receive when being closely examined by a strange doctor. The unfamiliar environment of a hospital or other treatment facility exacerbates the child's fears. The austere appearance of the unknown medical instruments may further scare the child. The child's apprehension may hinder both treatment and recovery.

The performance of an ear examination on a child is a good example. Ear examinations are often difficult to perform because the child tends to squirm or shy away from the otoscope being used to effect the examination. It is particularly important that a child remain motionless during an ear examination because the speculum of the otoscope must be precisely positioned with respect to the child's ear canal. However, this is often difficult to accomplish, because the appearance of the otoscope makes the child uneasy.

The importance of a child's psychological security during medical treatment is well recognized. Pre-treatment hospital visits are conducted to familiarize child patients with the environment they will be treated in. The workings of stethoscopes and other medical devices are explained to a child before being used, and children are often given a chance to use an instrument themselves to see how it works. Teddy bears are often given to children when receiving treatment to further instill a sense of security. But the appearance of the instruments used during the examination has heretofore not been modified for child care. In an effort to design instruments which psychologically reassure an adult, instruments have been designed with an appearance that may psychologically threaten a child. It is clear that there is an unfulfilled need in the prior art for medical instruments which do not appear as foreign and threatening to children.

SUMMARY OF THE INVENTION

Accordingly, it is an object of the invention to provide an otoscope or similar medical instrument having an appearance which is less threatening and foreign to small children than that of otoscopes which are presently in use.

In order to achieve these and other objects of the invention, an apparatus for performing a medical examination on a small child includes an instrument for performing the desired examination; and structure on the instrument for distracting the child prior to or during the examination, whereby the child will be less apprehensive about the examination while it is being performed.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
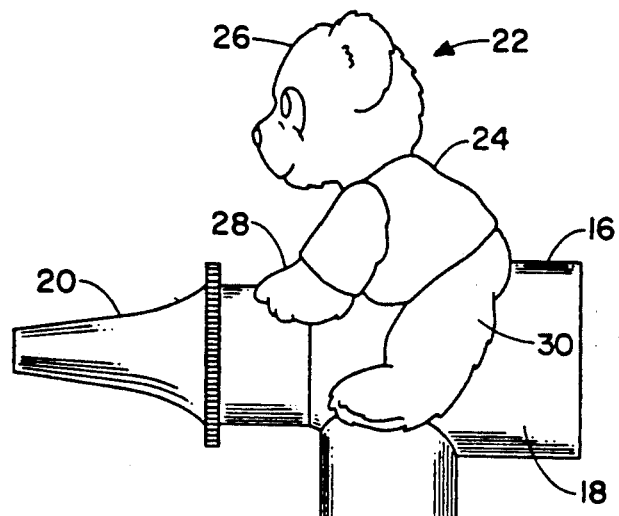
FIG. 1 is a side elevational view of an otoscope which is constructed according to a first embodiment of the invention.
Figure 2:
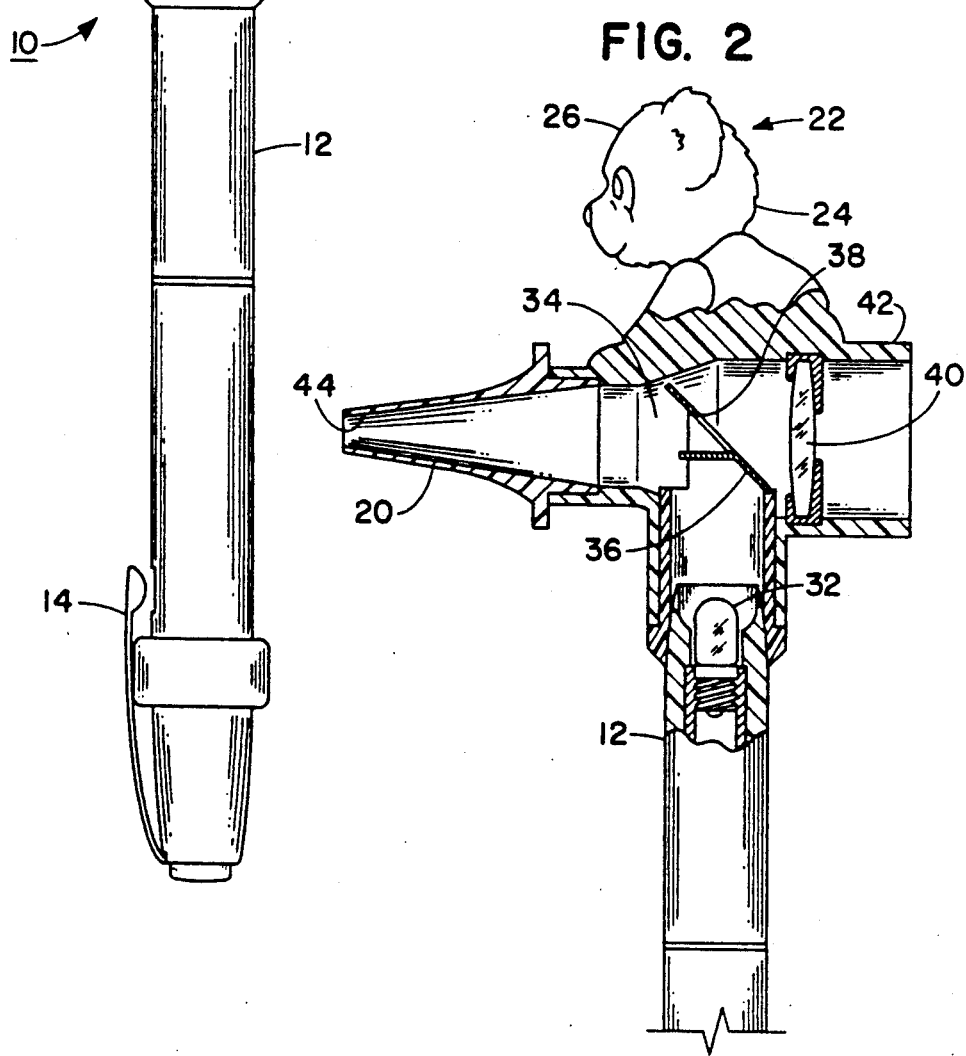
FIG. 2 is a fragmentary cross-sectional view taken through the embodiment of the invention which is illustrated in FIG. 1.

Referring now to the drawings, wherein like reference numerals designate corresponding structure throughout the views, and referring in particular to FIGS. 1 and 2, an improved otoscope 10 according to a first embodiment of the invention includes a handle portion 12 having a pocket clip 14, a viewing head 16 having a cylindrical outer surface 18 and a speculum 20 which is adapted for insertion into an ear canal of a patient. As may be seen in FIG. 1, a toy-like object 22 is provided on the otoscope 10 for distracting a child prior to or during an ear examination. In the embodiment depicted in FIGS. 1 and 2, the toy-like object 22 is shaped to resemble a bear 24 having a head 26, two arms 28 and two legs 30. Legs 30 are arranged so as to straddle the cylindrical outer surface 18 of the viewing head 16, as is best shown in FIG. 1. The arms 28 are likewise fastened to the cylindrical outer surface 18 of viewing head 16. The head 26 of bear 24 is arranged to face in the same direction as the speculum 20 projects from the viewing head 16. Preferably, bear 24 is integral with the viewing head 16, as is shown in cross section in FIG. 2. However, the bear 24 may also be removable from the viewing head 16, such as by fastening the legs 30 of bear 24 to the cylindrical outer surface 18 of viewing head 16 by a velcro-type fastener.

Looking now to FIG. 2, the handle 12 of the otoscope 10 includes a lamp 32 that is positioned within a T-shaped open space 34 that is defined in handle 12 and viewing head 16. A mirror element 36 is positioned within the open space 34 to reflect light from lamp 32 toward the speculum 20. Mirror element 36 is washer-shaped, having an inner edge 38 which defines a hole through which light may pass. Aligned with the hole which is defined by edge 38 is a lens element 40 that is mounted within the viewing head 16. The end portion of viewing head 16 which is proximate lens 40 has an opening defined therein through which an image may pass, and terminates in a shroud 42 for shading the opening.

When the otoscope 10 is in use, lamp 32 is caused to emit light, which is reflected by mirror element 36 through an opening 44 which is defined in a distal end of the speculum 20. This light will illuminate the ear canal of the patient that is being examined. The brightened image of the ear canal is then reflected back through the speculum 20, through the hole which is defined by the inner edge 38 of mirror element 36, through lens 40 where it is magnified for the benefit of the person who is performing the examination. Other specific details of the otoscope are well-known to those skilled in the art and are not considered essential to understand the invention.

Figure 3:
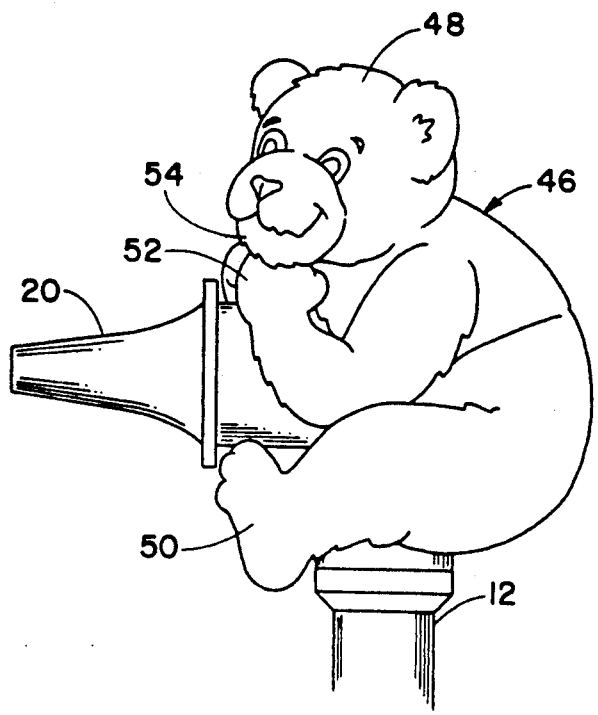
FIG. 3 is a fragmentary elevational view of an otoscope constructed according to a second embodiment of the invention.

Referring now to FIG. 3, an otoscope constructed according to a second embodiment of the invention is provided with a second type of bear 46 which has a head 48, a pair of legs 50, a pair of hands 52 and a chin 54. In this embodiment, legs 50 of the second bear 46 are straddled about the cylindrical outer surface 18 of the viewing head 16, and the hands 52 are in contact with the chin 54 of the bear 46. This gives the bear 46 a thoughtful posture which is particularly appealing to children.

Figure 4:
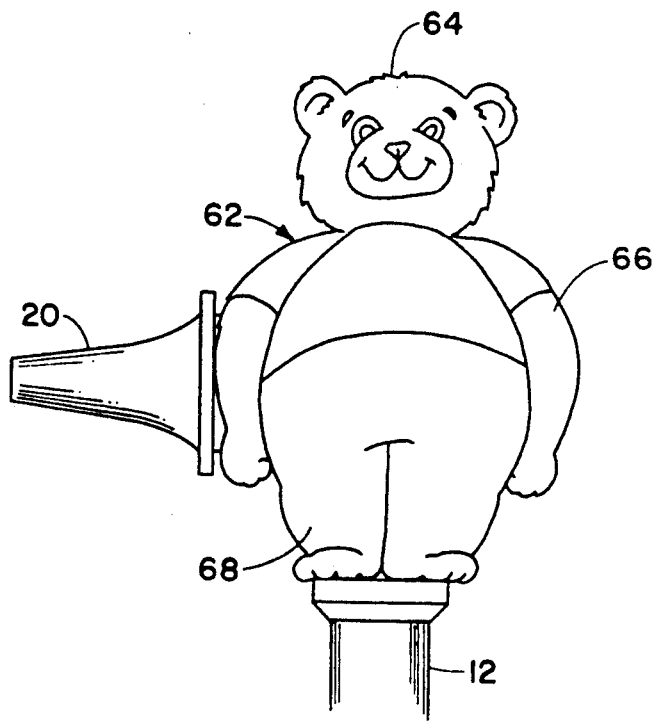
FIG. 4 is a side elevational view of an otoscope constructed according to a third embodiment of the invention.

Looking now to FIG. 4, a third embodiment of the invention includes a third bear 62 having a head 64, a pair of arms 66 and a pair of legs 68. In this embodiment, the bear 62 is positioned with its back in contact with the cylindrical outer surface 18 of the viewing head 16. In this embodiment, two bears may be mounted on the viewing head 16, one bear on each side of the viewing head.

Figure 5:
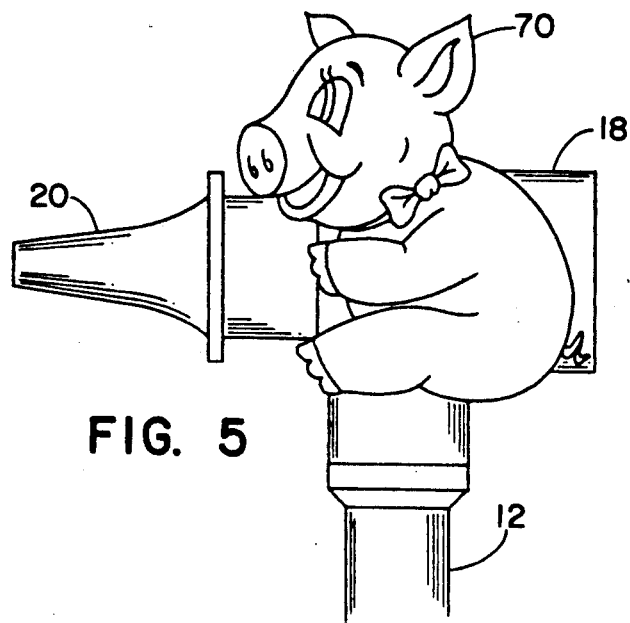
FIG. 5 is a fragmentary side elevational view of an otoscope constructed according to a fourth embodiment of the invention.

FIG. 5 illustrates a fourth embodiment of the invention, in which a pig 70 is mounted to the outer cylindrical surface 18 of the viewing head 16.

Figure 6:
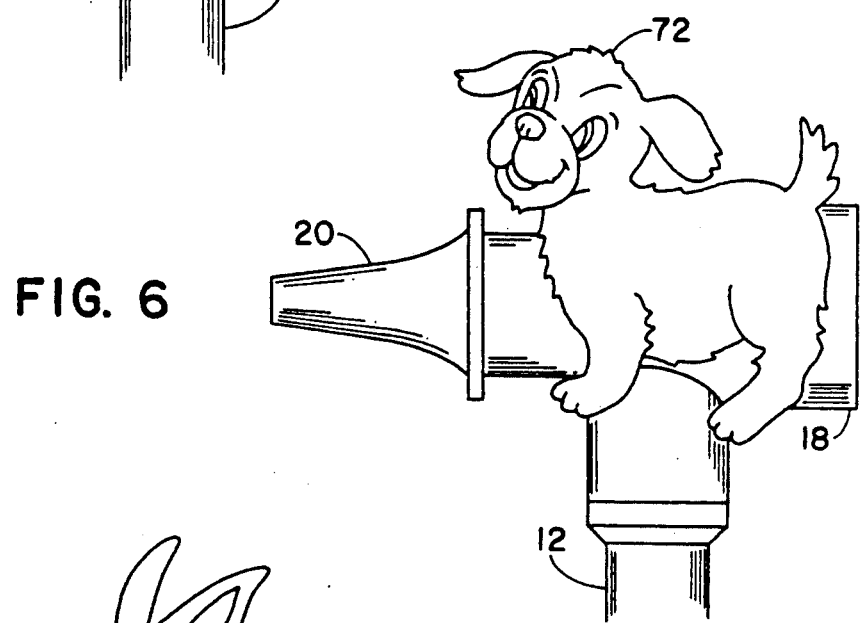
FIG. 6 is a fragmentary side elevational view of an otoscope constructed according to a fifth embodiment of the invention.

FIG. 6 illustrates a fifth embodiment of the invention, wherein a dog 72 is mounted to the outer cylindrical surface 18 of the viewing head 16.

Figure 7:
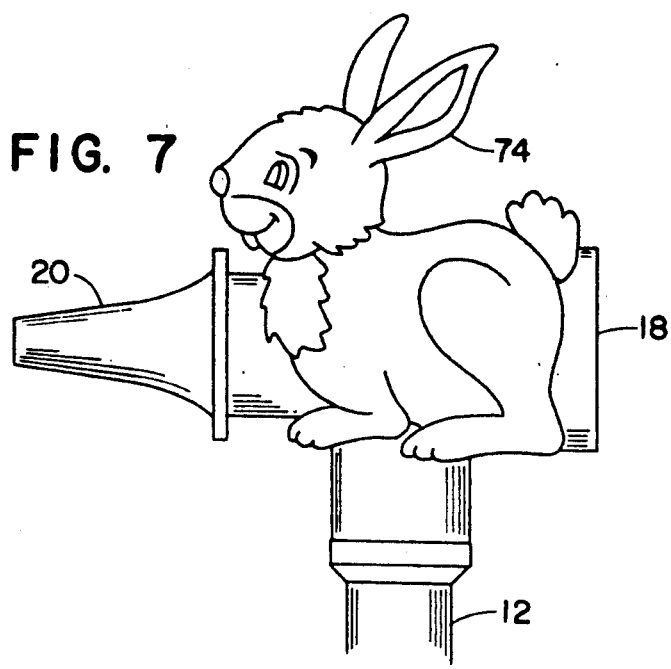
FIG. 7 is a fragmentary side elevational view of an otoscope constructed according to a sixth embodiment of the invention.

FIG. 7 illustrates a sixth embodiment of the invention, wherein a rabbit 74 is mounted to the outer cylindrical surface 18 of the viewing head 16.

Figure 8:
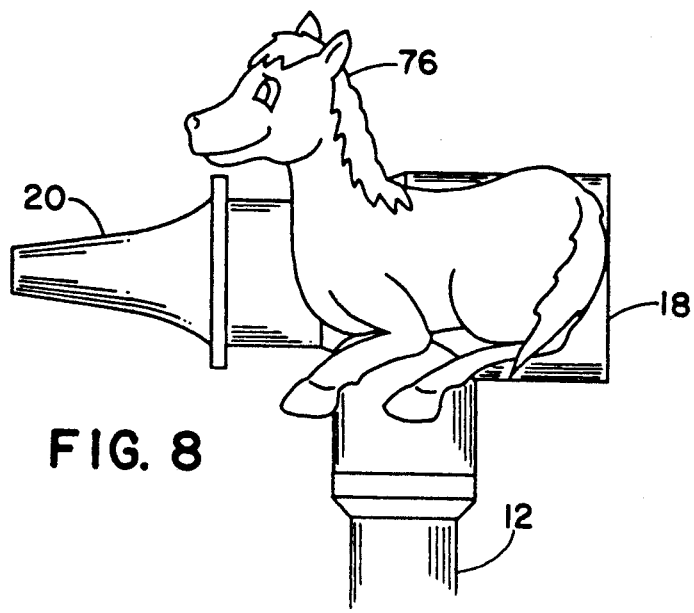
FIG. 8 is a fragmentary side elevational view of an otoscope constructed according to a seventh embodiment of the invention.

FIG. 8 illustrates a seventh embodiment of the invention, wherein a horse 76 is mounted to the outer cylindrical surface 18 of the viewing head 16.

Figure 9:
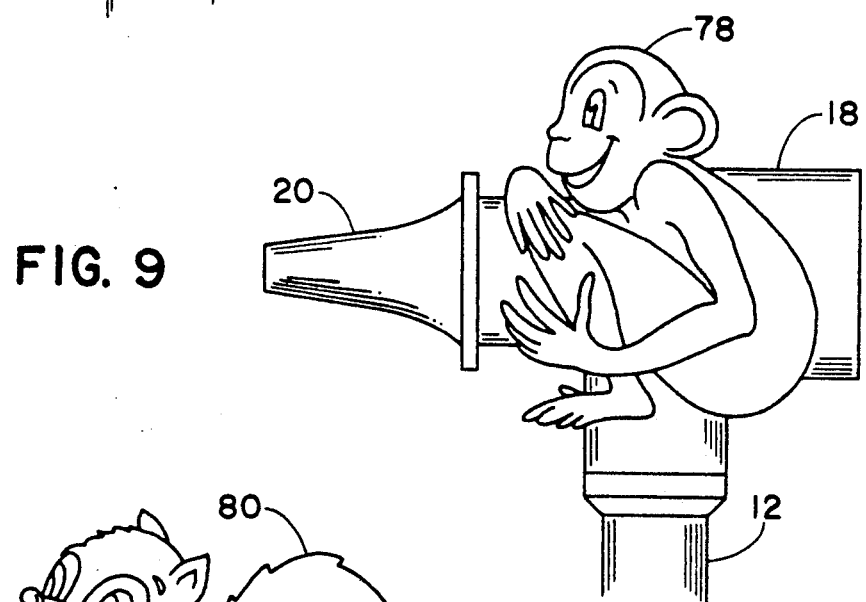
FIG. 9 is a fragmentary side elevational view of an otoscope constructed to an eighth embodiment of the invention.

FIG. 9 illustrates an eighth embodiment of the invention, wherein a monkey 78 is mounted to the outer cylindrical surface 18 of the viewing head 16.

Figure 10:
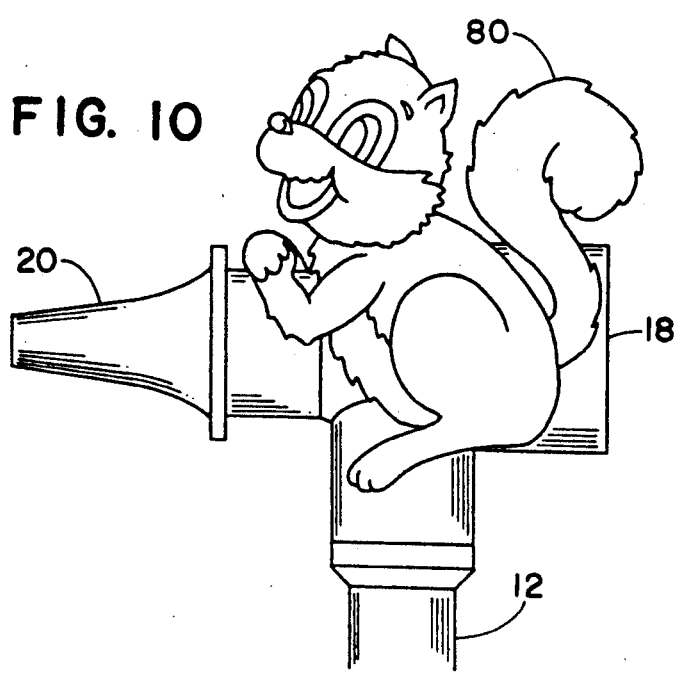
FIG. 10 is a side fragmentary elevational view of an otoscope constructed according to a ninth embodiment of the invention.

FIG. 10 illustrates a ninth embodiment of the invention, wherein a chipmunk 80 is mounted to the outer cylindrical surface 18 of the viewing head 16.

Figure 11:
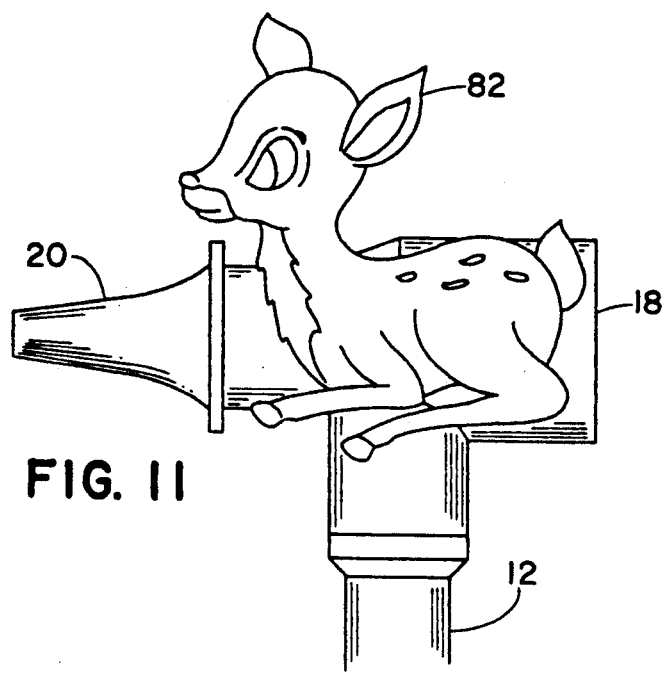
FIG. 11 is a fragmentary side elevational view of an otoscope constructed to a tenth embodiment of the invention.

FIG. 11 illustrates a tenth embodiment of the invention, wherein a deer 82 is mounted to the outer cylindrical surface 18 of the viewing head 16.

Figure 12:
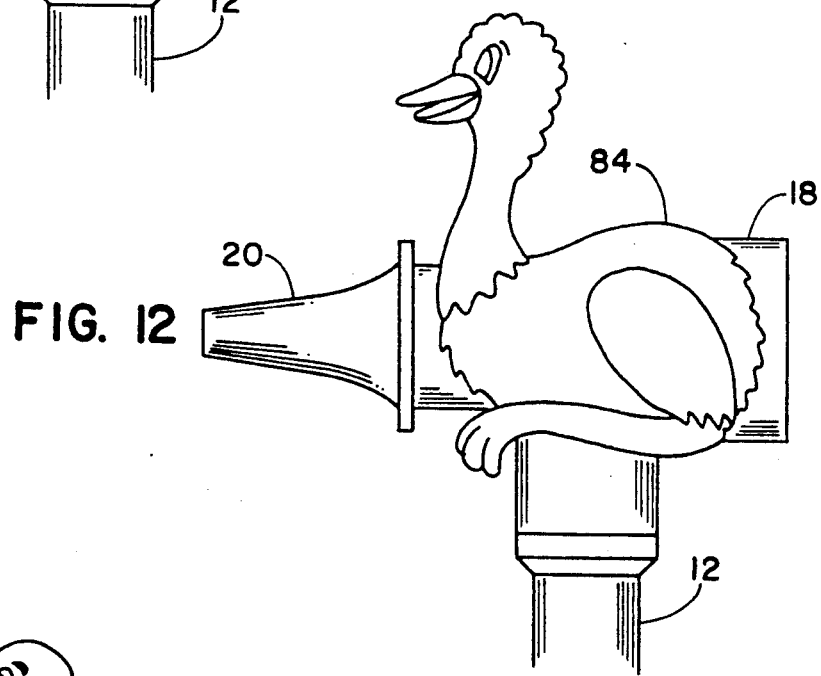
FIG. 12 is a fragmentary side elevational view of an otoscope constructed to an eleventh embodiment of the invention.

FIG. 12 illustrates an eleventh embodiment of the invention, wherein a goose 84 is mounted to the outer cylindrical surface 18 of the viewing head 16.

Figure 13:
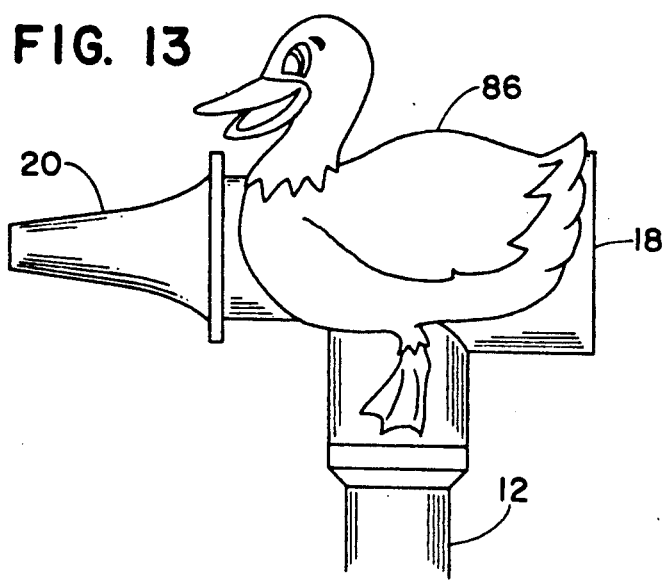
FIG. 13 is a fragmentary side elevational view of an otoscope constructed according to a twelfth embodiment of the invention.

Lastly, FIG. 13 illustrates a twelfth embodiment of the invention, wherein a duck 86 is mounted to the outer cylindrical surface 18 of the viewing head 16.

In operation, a health professional person will show the otoscope 10 to the child prior to performing an ear examination. Due to the presence of the toy-like object 22 on the otoscope 10, the otoscope 10 will appear to be less foreign and threatening to the child than another otoscope would be. During the examination, the child is less likely to be apprehensive, which will make the examination safer and more efficient to conduct.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An improved otoscope apparatus for performing an ear examination on a small child, comprising:
    an otoscope having a handle portion, a viewing head and a speculum attached to said viewing head, said speculum being adapted for insertion into the ear of a small child; and
    a toy-like object integrally molded to said viewing head of said otoscope for distracting the child prior to or during the examination, whereby the child will be less apprehensive about the examination while it is being performed.

2. An apparatus according to claim 1, wherein said toy-like object resembles a bear.

3. An apparatus according to claim 2, wherein said bear is positioned to straddle the instrument.

4. An apparatus according to claim 2, wherein said bear is positioned with its back to the instrument.

5. An apparatus according to claim 1, wherein said toy-like object resembles a pig.

6. An apparatus according to claim 1, wherein said toy-like object resembles a dog.

7. An apparatus according to claim 1, wherein said toy-like object resembles a rabbit.

8. An apparatus according to claim 1, wherein said toy-like object resembles a horse.

9. An apparatus according to claim 1, wherein said toy-like object resembles a monkey.

10. An apparatus according to claim 1, wherein said toy-like object resembles a chipmunk.

11. An apparatus according to claim 1, wherein said toy-like object resembles a deer.

12. An apparatus according to claim 1, wherein said toy-like object resembles a goose.

13. An apparatus according to claim 1, wherein said toy-like object resembles a duck.

* * * * *